(12) United States Patent
Ijitsu et al.

(10) Patent No.: US 9,044,556 B2
(45) Date of Patent: Jun. 2, 2015

(54) INJECTOR

(75) Inventors: Takanori Ijitsu, Fujimino (JP); Takaaki Ohsawa, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 859 days.

(21) Appl. No.: 12/892,612

(22) Filed: Sep. 28, 2010

(65) Prior Publication Data

US 2011/0040280 A1  Feb. 17, 2011

Related U.S. Application Data

(63) Continuation of application No. PCT/JP2009/056225, filed on Mar. 27, 2009.

(30) Foreign Application Priority Data

Mar. 28, 2008  (JP) ................................. 2008-086695

(51) Int. Cl.
  *A61M 5/315*  (2006.01)
  *A61M 5/46*  (2006.01)
  *A61M 5/32*  (2006.01)
  *A61M 5/31*  (2006.01)

(52) U.S. Cl.
  CPC ............. *A61M 5/46* (2013.01); *A61M 5/31501* (2013.01); *A61M 5/31505* (2013.01); *A61M 5/3287* (2013.01); *A61M 2005/3109* (2013.01)

(58) Field of Classification Search
  USPC .................................. 604/117, 218, 181, 187
  See application file for complete search history.

(56) References Cited

U.S. PATENT DOCUMENTS

| | | | |
|---|---|---|---|
| 4,886,499 | A | 12/1989 | Cirelli et al. |
| 6,045,534 | A | 4/2000 | Jacobsen et al. |
| 6,056,728 | A | 5/2000 | von Schuckmann |
| 7,108,679 | B2 | 9/2006 | Alchas |
| 2006/0229562 | A1 | 10/2006 | Marsh et al. |
| 2008/0154205 | A1 | 6/2008 | Wojcik |

FOREIGN PATENT DOCUMENTS

| | | |
|---|---|---|
| JP | 63-164963 A | 7/1988 |
| JP | 2000-506025 A | 5/2000 |
| JP | 2007-111537 A | 5/2007 |
| JP | 2007-528274 A | 10/2007 |
| WO | 2007/027203 A2 | 3/2007 |

OTHER PUBLICATIONS

International Search Report (PCT/ISA/210) issued on Apr. 21, 2009, by Japanese Patent Office as the International Searching Authority for International Application No. PCT/JP2009/056225.

*Primary Examiner* — Kevin C Sirmons
*Assistant Examiner* — Deanna K Hall
(74) *Attorney, Agent, or Firm* — Buchanan Ingersoll & Rooney PC

(57) ABSTRACT

An injector includes a support tube having one end surface to be brought into contact with skin, a movable tube advanceable in the support tube in the direction of the skin, an injection needle communicating with the movable tube, a plunger advanceable in the movable tube in the direction of the skin to introduce medicinal liquid filled in the movable tube to the injection needle, and a sealing material provided at the tip of the support tube and penetratable by the injection needle to penetrate the sealing material. In an initial state, the tip of the injection needle is sealed by the sealing material.

20 Claims, 7 Drawing Sheets

INJECTOR

This application is a continuation of International Application No. PCT/JP2009/056225 filed on Mar. 27, 2009, and claims priority to Japanese Application No. 2008-086695 filed on Mar. 28, 2008, the entire content of both of which is incorporated herein by reference.

TECHNICAL FIELD

The present invention generally pertains to a medicine injector. More specifically, the invention relates to a medicinal liquid injector configured to regulate the puncture depth of an injection needle.

BACKGROUND DISCUSSION

A human skin is composed of a epidermis and a dermis in this order from the surface side. On the lower side of the skin is a subcutaneous tissue, such as a fat layer, and muscular tissue. Intracutaneous injection is an injection into the epidermis or the dermis, and subcutaneous injection is an injection into the subcutaneous tissue. The intracutaneous injection and the subcutaneous injection are selected according to the kind of medicinal liquid and the purpose of the injection.

Since the epidermis and the dermis are comparatively thin, it may not always be easy for an unskilled person to achieve the subcutaneous or intracutaneous injection desired. For this reason, injectors have been proposed in which the advancement of the injection needle in the direction of the skin can be limited by a predetermined stopper so as to control the depth of puncture. Examples of these injectors are disclosed in Japanese Patent Publication No. 2648314 and Japanese Application Publication No JP-T-2007-528274.

Though the injector allows regulation of the puncture depth of the injection needle, the injector is unstable during injection and may not maintain a constant puncture depth.

In addition, such an injector requires the implement to be filled with a medicinal liquid prior to injection, which renders the injector unsuited to so-called prefilled injectors. Further, such an injector is relatively complicated in structure.

Since the just-mentioned type of injector is not of the prefilled type, it requires much effort and attention for filling the implement with a proper amount of medicinal liquid accurately, and needs appropriate control of the medicinal liquid separate from the injector. Therefore, with such an injector, for example, it is difficult for a patient who is weak-sighted or who is not deft to inject a medicinal liquid by himself or herself.

SUMMARY

The disclosed injector is relatively simple in structure and operation, is useful as a prefilled type, and enables accurate regulation of the puncture depth of an injection needle.

The injector comprises: a support tube possessing an end face to be pressed against skin; a movable tube positioned in the support tube and advanceable in the support tube toward the skin; an injection needle provided with a lumen, the lumen having a rear end opening at a rear end of the needle which communicates with the movable tube and a tip end opening at a tip end of the opening from which medicinal liquid is to be ejected; and a plunger positioned in the movable tube and advanceable in the movable tube toward the skin to cause medicinal liquid in the movable tube to be guided into the injection needle. A sealing material at a tip of the support tube is penetrable by the injection needle, and a stopper limits advancement of the movable tube in the support tube to a predetermined position. In an initial state of the injector, the tip end opening of the injection needle is sealed by the sealing material.

Notwithstanding its relatively simple structure, the injector is configured such that by a simple operation of pushing the movable tube into the support tube, the movement can be limited by the stopper at the time when the puncture depth of the injection needle has reached a proper length (depth). In the initial state, the tip opening of the injection needle is sealed by the sealing material, and this is well suited for the prefilled type injector.

Relative movements of the support tube and the movable tube may be guided by an axially extending guide to facilitate stable operation. Also, the tip of the support needle can be provided with a flange having a hole through which the injection needle is to be passed, and the sealing material may be in contact with the flange. Such a flange helps enable stable contact of the injector with the skin.

A pressure-sensitive adhesive may be provided on the surface of the flange which makes contact with the skin. Such a pressure-sensitive adhesive enables secure contact of the injector with the skin, further facilitating stable operation can be performed and accuracy of the puncture depth of the injector is enhanced. In addition, the pressure-sensitive adhesive prevents leakage of the medicinal liquid, so that an accurate amount of the medicinal liquid can be injected.

The periphery of the through hole in the flange may be protuberant toward the skin to facilitate enhanced secure contact performance (adhesion) between the injector and the skin.

The injector may have first fixing means for fixing the movable tube to the support tube in the initial state. The first fixing means prevents the movable tube from being moved inadvertently, so that the tip of the injection needle can be prevented from slipping off the sealing material. The injector may also have second fixing means for fixing the plunger to the movable tube in the initial state. The second fixing means prevents the plunger from being moved inadvertently, so that the medicinal liquid inside the movable tube is prevented from leaking out.

The tip face of the support tube may be arranged non-perpendicular to the axial direction of the support tube so that the support tube makes contact with the skin obliquely. This allows oblique injections to be carried out according to the kind and purpose of the procedure.

According to another aspect, an injector includes: a support tube having a hollow interior and possessing an end face at a distal end of the support tube to be pressed against skin; a movable tube positioned in the support tube, the movable tube possessing a hollow interior and a distal end; a medicinal fluid in the movable tube; an injection needle connected to the distal end of the movable tube so that the movable tube and the injection needle move together as a unit, wherein the injection needle extends in the distal direction from the distal end of the movable tube and possesses a sharp distal end, and with the needle including a lumen having a rear end opening which opens into the hollow interior of the movable tube and a tip end opening at the sharp distal end of the needle from which the medicinal liquid is ejected; a plunger in the hollow interior of the movable tube and movable in the distal direction toward the distal end of the movable tube to deliver the medicinal liquid in the movable tube into the lumen of the injection needle; a sealing material at the distal end of the support tube, with the sharp distal end of the injection needle being embedded in the sealing material so the tip end opening of the lumen of the injection needle is closed by the sealing material to prevent the medicinal fluid in the movable tube from flowing out the tip end opening of the lumen of the injection needle. The movable tube is movable within the hollow interior of the support tube to move in a distal direction relative to the support tube from an initial position in which the sharp distal end of the injection needle is embedded in the sealing material to a puncture position in which the sharp distal end of the injection needle is positioned distally of the sealing material and distally of the end face of the support tube to puncture the skin. A stopper is provided on at least one of the support tube and the movable tube to stop the movement of the movable tube in the distal direction relative to the support tube so the movable tube is at the puncture position.

Another aspect involves a method of operating an injector which is in an initial position. The injector in the initial position comprises a movable tube movably positioned in a support tube, an injection needle fixed to the movable needle to move together with the movable needle, a plunger positioned in the movable tube, medicinal fluid in the movable tube, and a sealing material at a tip of the support tube, wherein the injection needle possesses a sharp distal end and a distal end opening which opens into a lumen communicating with the medicinal fluid in the movable tube, and the sharp distal end of the injection needle being embedded in the sealing material so the distal end opening of the lumen of the injection needle is closed by the sealing material to prevent the medicinal fluid in the movable tube from flowing out the distal end opening of the lumen of the injection needle in the initial position. The method involves: pressing a distal end face of the support tube against skin to be punctured; moving the movable tube in a distal direction relative to the support tube to cause the sharp distal end of the injection needle to move in the distal direction, pass completely through the sealing material so that the distal end opening is no longer closed by the sealing material, and extend distally beyond the distal end face of the support tube to puncture the skin; and moving the plunger in the distal direction relative to the movable tube to force the medicinal fluid in the movable tube into the injection needle and to thereby inject the medicinal fluid in the skin.

BRIEF DESCRIPTION OF THE DRAWING FIGURES

DETAILED DESCRIPTION

The injector disclosed here is described below with reference to several embodiments shown in FIGS. 1-7. In the following description, the upward and downward directions are based on the condition or orientation shown in FIGS. 1-6, but it is to be understood that in practical use, the direction of the injector 10 is not limited.

Figure 1:
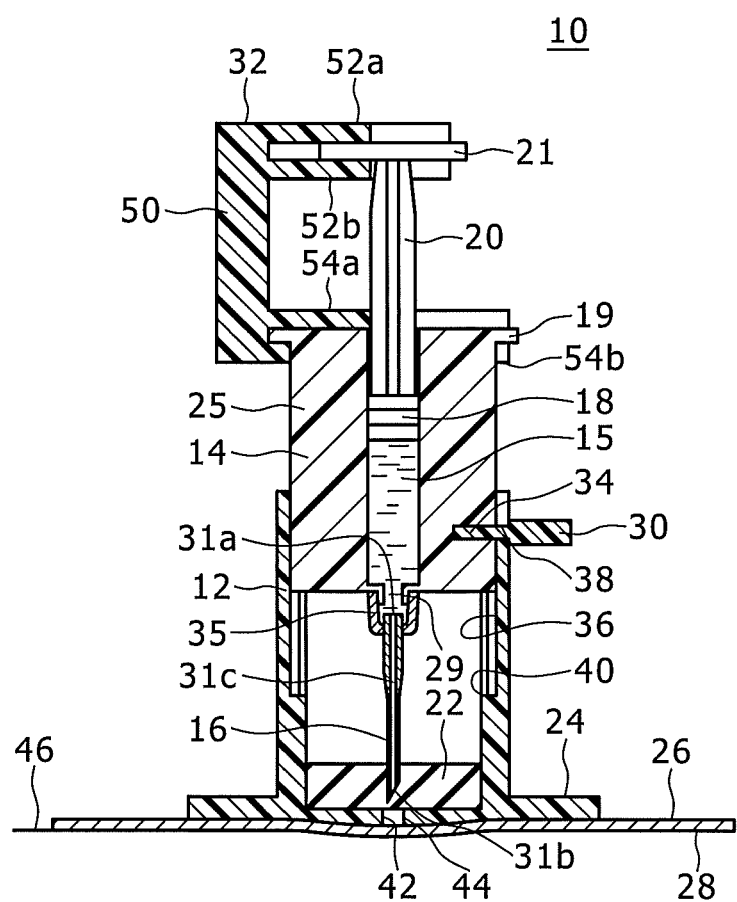
FIG. 1 is a cross-sectional side view of an injector according to one disclosed embodiment.
Figure 2:
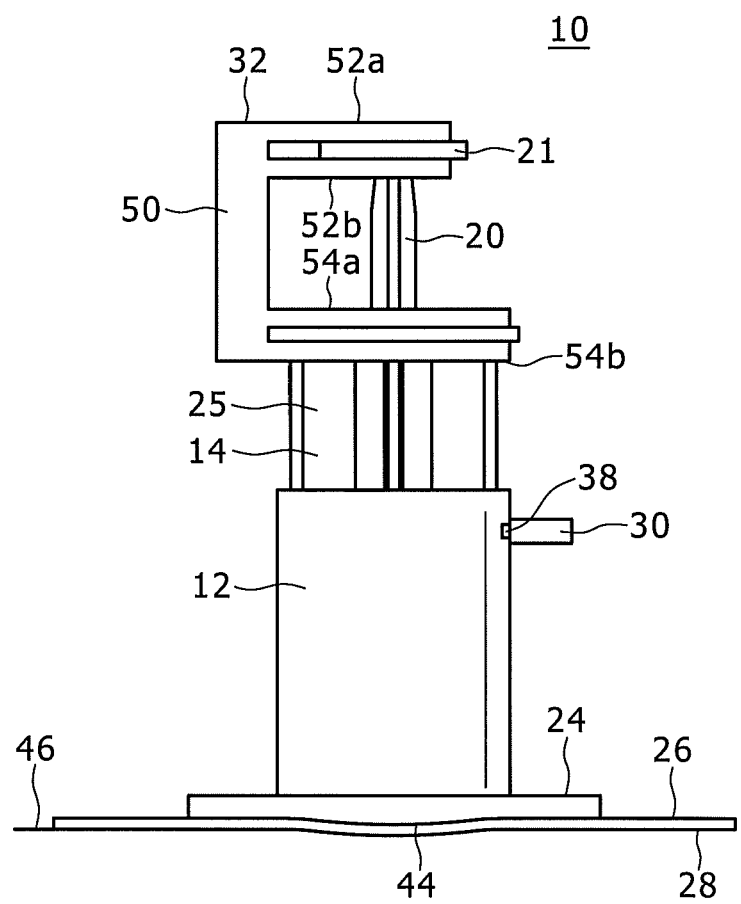
FIG. 2 is a side view of the injector shown in FIG. 1.
Figure 3:
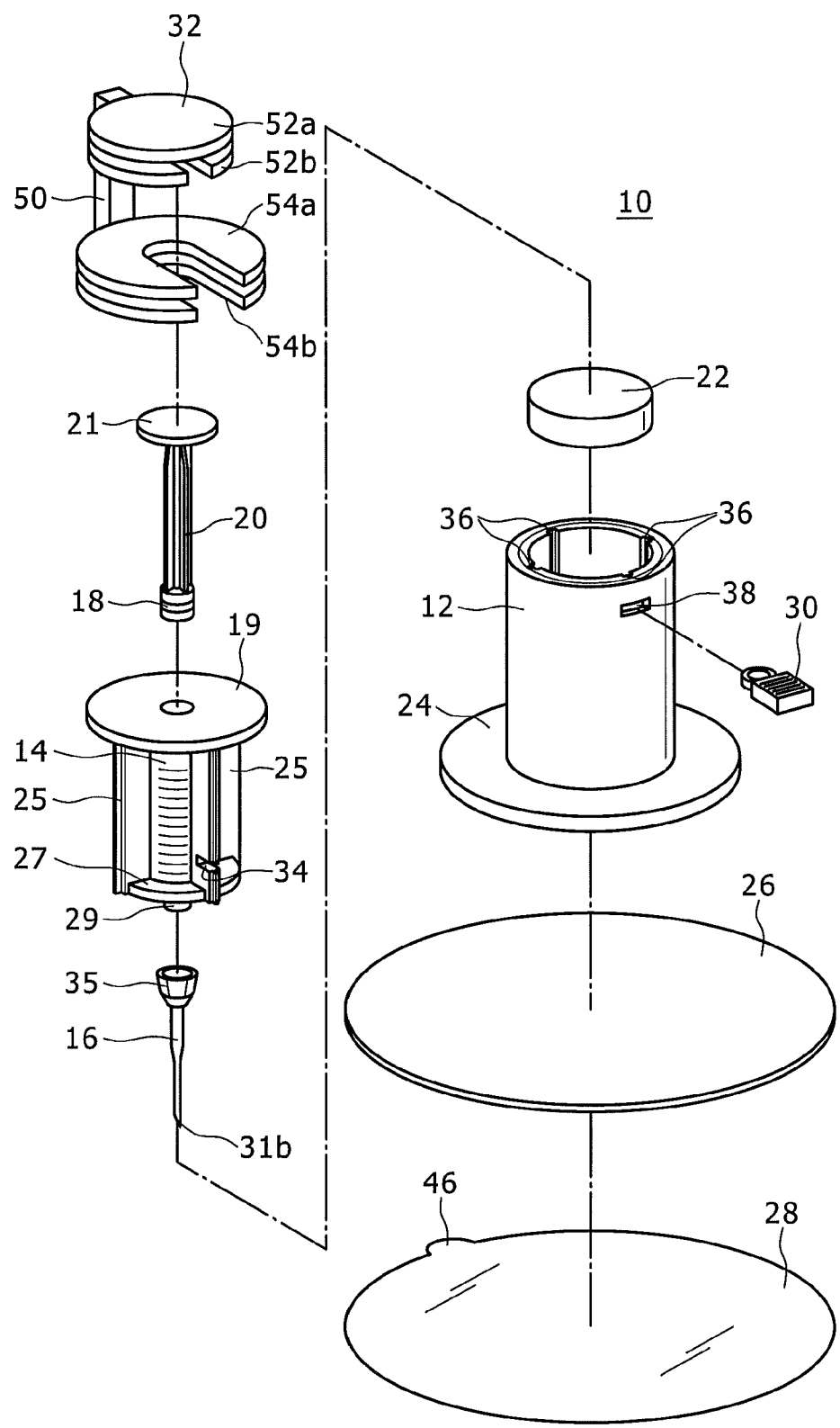
FIG. 3 is an exploded perspective view of the injector illustrated in FIG. 1.

As shown in FIGS. 1, 2 and 3, the injector 10 according to one embodiment disclosed here includes: a support tube 12 having one end face adapted to be brought into contact with skin of a living body; a movable tube 14 positioned in the support tube 12 and advanceable in the support tube 12 toward the skin; an injection needle 16 configured to communicate with and move together with the movable tube 14; a plunger 20 positioned in the movable tube 14 and advanceable in the movable tube 14 toward the skin such that medicinal liquid 15 in the movable tube 14 is guided into the injection needle 16; a sealing material 22 provided at the tip (distal end) of the support tube 12 and penetrable by the injection needle 16; a flange 24 at the distal tip of the support tube 12; a pressure-sensitive adhesive 26 on that lower surface of the flange 24 which is adapted to make contact with the skin; and a protective film 28 adhered to a pressure-sensitive adhesive surface on the lower side of the pressure-sensitive adhesive 26. The injection needle 16 possesses a lumen $31c$ through which the medicinal liquid passes. The lumen $31c$ includes a rear end opening (proximal opening) $31a$ and a tip end opening (distal opening) $31b$ at the sharp distal end of the needle. The term "medicinal liquid" is used in a broad sense inclusive of medical supplies such as vaccines, hormones, sedatives and the like, and nutritional supplements.

In an initial state shown in FIG. 1, the tip opening $31b$ of the injection needle 16 is sealed by the sealing material 22. That is, the distalmost end of the needle 16 does not extend distally beyond the distalmost end of the sealing material 22. Stated differently, the distalmost end of the needle 16 is spaced proximally of the distalmost end of the sealing material 22.

The injector 10 also includes a first fixture (first fixing means) 30 for fixing the movable tube 14 to the support tube 12 in the initial state, and a second fixture (second fixing means) 32 for fixing the plunger 20 to the movable tube 14 in the initial state.

A gasket 18 is positioned at the lower end of the plunger 20, and a small flange 21 for performing a pressing operation is provided at the upper end of the plunger 20. The plunger 20 is a typical known plunger used with injectors.

The movable tube 14 is a member corresponding to a syringe body in a normal injector. As best seen in FIG. 3, the movable tube 14 includes a finger hold plate 19 at the upper end of the tube 14, four axially extending and radially outwardly directed ribs (guides) 25 circumferentially spaced apart at regular intervals on the peripheral surface of the tube 14, a small flange 27 at the lower end of the tube 14, and a connection part 29 projecting downward (axially) from the one end (lower end) of the tube 14. One of the ribs 25 is provided with a hole or cutout 34 for engagement with the first fixture 30. The movable tube 14 is transparent, and is provided with graduations on its side surface. A hub 35 of the injection needle 16 is fixed to the connection part 29 by adhesion, fusing, fitting or the like. The injection needle 16 is a hollow tapered needle, which is ordinarily used for insulin injectors.

The support tube 12 is transparent, and is configured to include a lumen in which is slidably support the movable tube 14. The support tube 12 has four inwardly facing and axially extending guide grooves 36 configured and sized to engage the ribs 25, and a fixing through hole 38 in its side surface in which is to be inserted the first fixture 30. The guide grooves 36 extend axially along the lumen of the support tube 12, from the upper end to an intermediate part of the support tube 12, and cooperate with the ribs 25 to help guide stable relative movements of the support tube 12 and the movable tube 14 in the axial direction. Stepped parts (stopper) 40 at the lower ends of the guide grooves 36 serve as a stopper for limiting/ stopping the advancement of the movable tube 14 so that the movable tube 14 stops at a predetermined position relative to the support tube 12. The stoppers 40 are, in essence, the end point of the grooves 36. The stepped parts 40 are so set that the amount by which the injection needle 16 projects beyond the pressure-sensitive adhesive 26 when the ribs 25 abut on the stepped parts 40 will be a prescribed length. The prescribed length is set according to such factors as the kind of procedure such as subcutaneous injection, intracutaneous injection, etc., the amount and kind of medicinal liquid 15, etc.

The sealing material 22 possesses a cylindrical shape and is fixed at the lower end of the lumen part of the support tube 12. In the initial state, the distal tip of the injection needle 16 pierces (i.e., is held in) the sealing material 22 to a substantially axially central portion of the sealing material 22 so that the injection needle 16 is sealed with the sealing material 22. Thus, in the initial state, the sharp distal end of the injection needle 16 is embedded in the sealing material 22 so that the tip end opening (distal opening) 31*b* of the lumen is closed. This prevents medicinal fluid in the movable tube 14 from leaking out of the distal end opening 31*b*. The sealing material 22 is, for example, a rubber body (silicone rubber, butyl rubber, or the like).

At a more distal portion of the support tube 12, the flange 24 is fixed integrally. The flange 24 is larger (for example, by a factor of about 2) in diameter than the support tube 12. The central portion of the flange 24 (end face of the support tube) has a relatively small through hole 42 for permitting passage of the injection needle 1. The axis of the through hole 42 and the axis of the needle 16 are aligned (coaxial). In addition, a protuberant part 44 surrounds the hole 42 and protrudes slightly toward the skin in the periphery of the hole 42. Since the protuberant part 44 surrounding the hole 42 protrudes axially in the direction of the skin, secure contact between the injector 10 and the skin is enhanced. The flange 24 and the sealing material 22 are in contact with each other, without any gap therebetween. Such a flange 24 helps ensure stable contact of the injector 10 with the skin.

The radius of curvature of the protuberant part 44 is not particularly limited. By way of example, the radius of curvature may be 6 to 200 mm, preferably 10 to 100 mm, more preferably 20 to 60 mm.

The pressure-sensitive adhesive 26 is formed from a soft material possessing a relatively small thickness so that it is penetrable by the injection needle 16, is larger (for example, by a factor of about 2) in diameter than the flange 24, and is fixed to the flange 24. The pressure-sensitive adhesive 26 is preferably a pressure-sensitive adhesive based on rubber, acryl, silicone or the like. Examples of the pressure-sensitive adhesive include pressure-sensitive hot-melt type ones and crosslinking type ones. The shape of the pressure-sensitive adhesive 26 may be one which promises relatively easy grasping of the location of puncture, such as a circle, an ellipse, a star shape, etc. The lower surface of the pressure-sensitive adhesive 26 is a pressure-sensitive adhesive surface to which the protective film 28 is adhered in the initial state, whereby pressure-sensitive adhesiveness (stickiness) is maintained. A small peel tab 46 projects from the protective film 28 so that the protective film 28 can be peeled from the pressure-sensitive adhesive 26.

The first fixture 30 is pin-shaped and engages the cutout 34 in the movable tube 14 through the fixing hole 38 in the initial state. As a result, the movable tube 14 is prevented from being inadvertently moved, and the tip of the injection needle 16 can be prevented from slipping off the sealing material 22. It should be appreciated that the first fixture 30 need not necessarily be an independent component part. For example, the support tube 12 and the movable tube 14 may be fixed to each other at parts constituting a fixation part, and the fixation part is cut to separate the tubes 12 and 14 from each other at the time of use. The same applies also to the second fixture 32.

The second fixture 32 includes a first holder which holds a portion of the plunger 20 and a second holder which holds a portion of the movable tube 14, wherein the first and second holders are connected to one another to fix the relative position of the plunger in the movable tube 14. In the illustrated embodiment, the second fixture 32 includes an axially extending rod 50, clamp plates 52*a*, 52*b* positioned at the upper end portion of the rod 50 and extending outwardly away from the rod 50 for clamping the upper and lower sides of the small flange 21, and clamp plates 54*a*, 54*b* at the lower end of the rod 50 and extending outwardly away from the rod 50 for clamping the upper and lower sides of the finger hold plate 19. The clamp plates 52*b*, 54*a*, 54*b* possesses notches and are substantially U-shaped to avoid interference with parts of the plunger 20 and the movable tube 14. The second fixture 32 can keep the plunger 20 fixed to the movable tube 14 in the initial state, whereby the plunger 20 is prevented from being moved inadvertently and the medicinal liquid 15 inside the movable tube 14 is prevented from leaking out.

The injector 10 is assembled as shown in FIG. 1 in the initial state for performing an injection, and the movable tube 14 is preliminarily filled with a prescribed amount of medicinal liquid 15. The injector 10 is thus a so-called prefilled type injector. The medicinal liquid 15 is sealed by the sealing material 22 and the gasket 18. In the initial state, the first fixture 30 and the second fixture 32 are mounted in predetermined positions, whereby relative movements of the support tube 12 and the movable tube 14, and relative movements of the movable tube 14 and the plunger 20, are prevented from occurring.

As is clear from FIGS. 1-3, the injector 10 is relatively simple in structure. The injector 10 is preliminarily sterilized or is produced in a substantially aseptic condition, and is packaged so that the sterilized state or the aseptic condition is maintained. After use, the injector 10 is discarded in a predetermined manner. Thus, the injector 10 is a disposable product.

The operation of the injector 10 configured as above will be described.

First, the protective film 28 is peeled off of the pressure-sensitive adhesive 26 by gripping and pulling the peel tab 46, and the injector 10 is then adhered to a predetermined part of a skin by pressing the exposed pressure-sensitive adhesive 26 against the skin. The injector 10 is stabilized by the pressure-sensitive adhesive effect of the pressure-sensitive adhesive 26 and the large-area flange 24, and is fixed in secure contact with the skin. In addition, by virtue of the protuberant part 44 of the flange 24, the site of puncture is pressed to an appropriate degree, whereby secure contact performance is enhanced. As a result, when the injection needle 16 comes into contact with the skin, the skin does not evade, and the needle point is permitted to advance into the skin swiftly.

Figure 4:
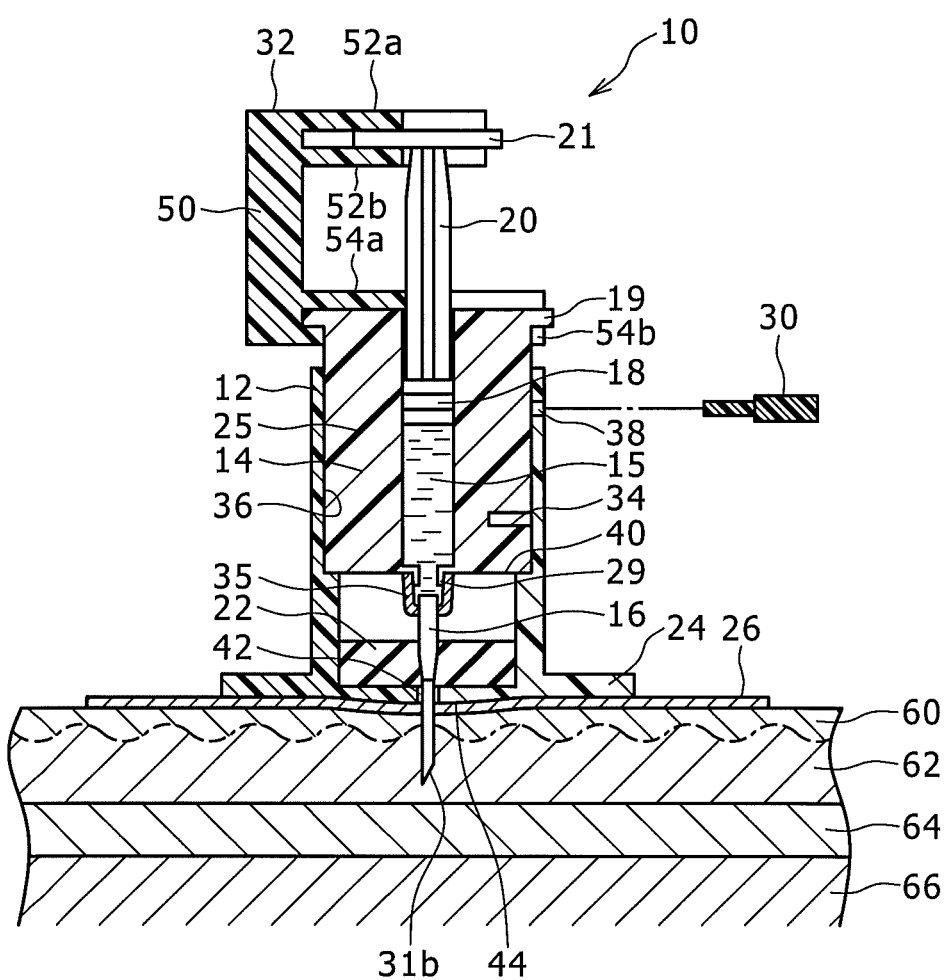
FIG. 4 is a cross-sectional side view of the injector shown in FIG. 1 in use while puncturing a living body.

Next, as shown in FIG. 4, the first fixture 30 is removed, and the movable tube 14 is pushed down until the ribs 25 abut on the stepped parts 40. As a result, the injection needle 16 penetrates the sealing material 22, passes through the hole 42, and penetrates the pressure-sensitive adhesive 26, to puncture the skin. For example, in the case of an intracutaneous injection, the needle point of the injection needle 16 further passes through the epidermis 60 of the skin to reach a dermis 62, but does not reach a subcutaneous tissue 64. Thus, the needle point is stopped when the puncture depth has reached an appropriate amount. The injection needle 16 is appropriately pressed by the sealing material 22, and is frictionally engaged, whereby the needle is kept stable.

In the case of a subcutaneous injection, the needle point of the injection needle 16 passes through the epidermis 60 and the dermis 62 to reach the fat layer 64, but does not reach the muscular tissue 66. Thus, the needle point is stopped when the puncture depth reaches an appropriate depth. In the case of a subcutaneous injection, the injector 10 can be appropriately configured to reach the fat layer, for example with a needle of appropriate length or with the height of the parts 40 adequately altered.

In addition, since the second fixture 32 is kept mounted at this point in time, the plunger 20 is prevented from moving relative to the movable tube 14, so that the medicinal liquid 15 in the movable tube 14 is prevented from leaking to the epidermis 60, the dermis 62 or the like.

Figure 5:
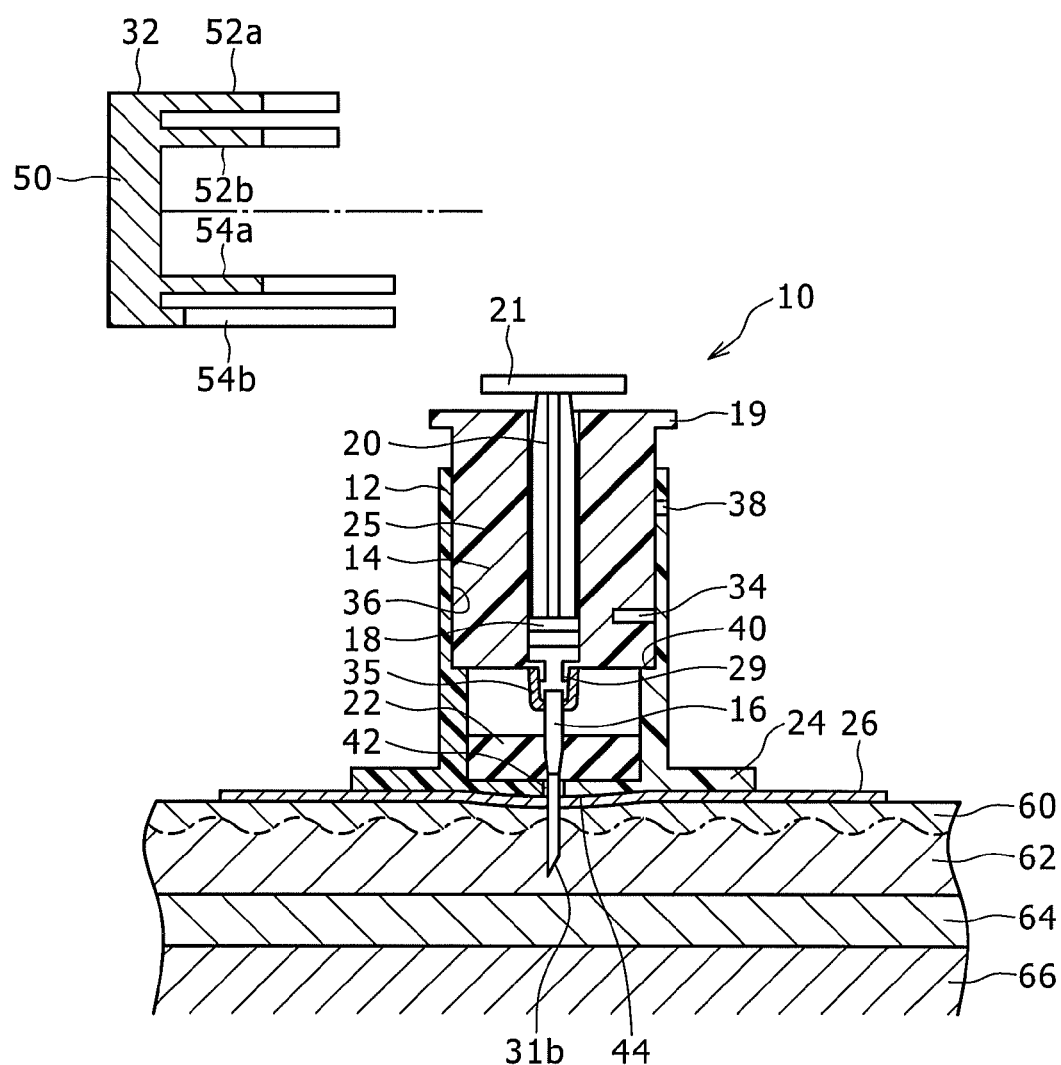
FIG. 5 is a cross-sectional side view of the injector shown in FIG. 1 during use while injecting a medicinal liquid into the living body.

After the second fixture 32 is removed, as shown in FIG. 5, the plunger 20 is pushed down until the gasket 18 abuts on the lower surface of the movable tube 14. As a result, the medicinal liquid 15 is guided out into the injection needle 16, and is injected into the living body. Here, since the injector 10 is set stable by the effects of the flange 24 and the pressure-sensitive adhesive 26 and the puncture depth of the injection needle 16 is kept appropriate, a prescribed amount of the medicinal liquid 15 can be injected to a desired depth. The pressure-sensitive adhesive 26 functions as an anti-leaking agent to help ensure accurate injection of the medicinal liquid 15.

In the case of an intracutaneous injection, the needle point of the injection needle 16 only reaches the epidermis 60 or the dermis 62, and the distance from the reached position to the surface of the skin is relatively short, but the secure contact of the pressure-sensitive adhesive 26 with the skin in a covering manner produces an anti-leaking effect. Therefore, the medicinal liquid 15 is inhibited or prevented from leaking out to the skin surface, and a prescribed amount of the medicinal liquid 15 can be injected accurately.

In performing injection, it is recommendable to look at the graduations on the movable tube 14 and thereby regulate the rate of injection. In using the injector 10, basically, the medicinal liquid 15 inside is wholly injected into a living body. Depending on conditions, however, just a certain amount (less than all) of the medicinal liquid 15 may be injected while looking at the graduations.

Thereafter, the injector 10 is detached from the skin, to complete the injection procedure.

As above-mentioned, even though the disclosed injector 10 possesses a relatively simple construction, the injection can be performed by the simple operation of pushing the movable tube 14 into the support tube 12, with the motion being limited by the stepped parts 40 when the puncture depth of the injection needle 16 has reached an appropriate length. Also, in the initial state, the tip opening 13b of the injection needle 16 can be sealed with the sealing material 22, which is suitable for the prefilled type. Since the injector 10 is of the prefilled type and enables an appropriate amount of a medicinal liquid to be accurately injected into the implement, for example, it permits a patient who is weak-sighted or who is not deft to inject a medicinal liquid by himself or herself.

Figure 6:
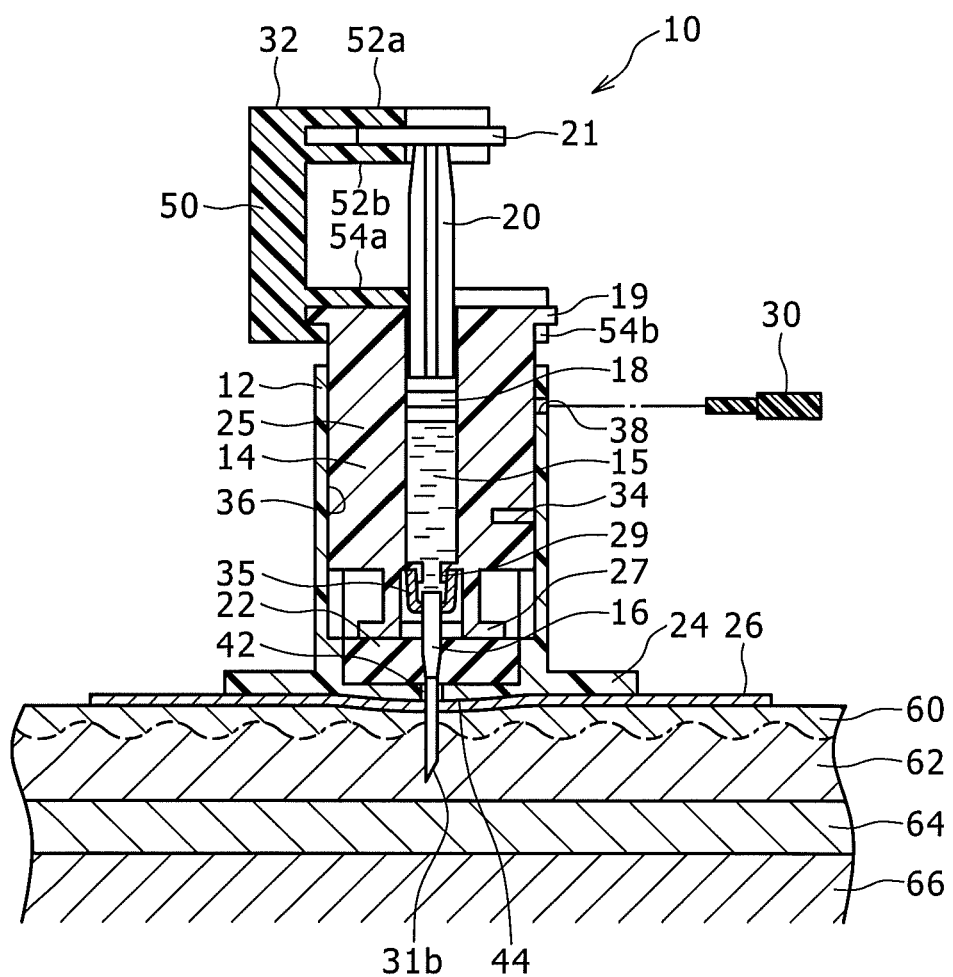
FIG. 6 is a cross-sectional side view of an injector according to a first modification.

The stopper for limiting the advancement of the movable tube 14 is not limited to the stepped parts 40. For example, as shown in FIG. 6, a small flange 27 forming a part of the movable tube 14 may abut on the upper surface of the sealing material 22. Alternatively, a part of the finger hold plate 19 may abut the upper surface of the support tube 12. The stopper for limiting the advancement of the movable tube 14 is not limited to a stationary type, but may be of the type in which the puncture depth can be regulated. In addition, a projected part or parts may be provided in the direction of the outer circumference of the guide grooves 36 and the ribs 25, whereby the movable tube 14 can be locked in a predetermined position.

Figure 7:
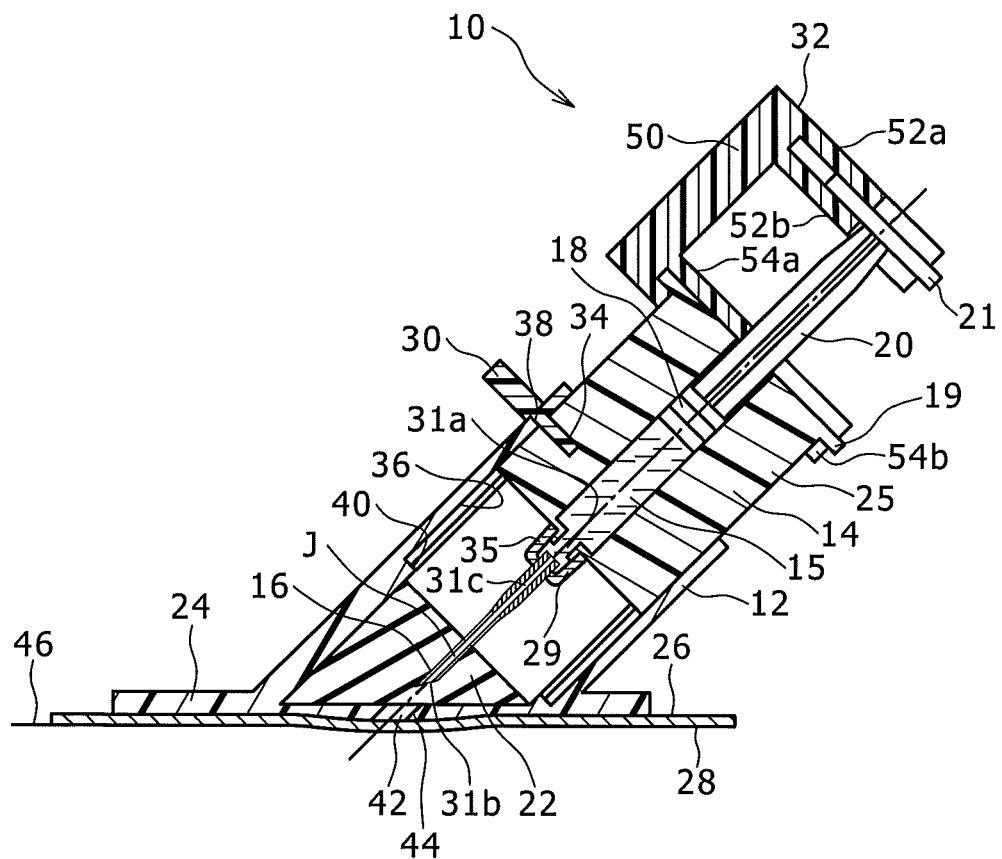
FIG. 7 is a cross-sectional side view of an injector according to a second modification.

As shown in FIG. 7, the flange 24 at the tip end face of the support tube 12 may be non-perpendicular to the direction of the axis J so that the support tube 12 makes contact with a skin obliquely. With the injector 10 according to such a modification, oblique injection (the needle is obliquely oriented relative to the skin) can be carried out according to the kind and purpose of the procedure. Oblique puncture facilitates adjustment of puncture depth.

The detailed description above describes embodiments of the injector and manner of use. The invention is not limited, however, to the precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An injector comprising:
    a support tube having a hollow interior and possessing an end face at a distal end of the support tube to be pressed against skin;
    a movable tube positioned in the support tube, the movable tube possessing a hollow interior and a distal end;
    a medicinal fluid in the movable tube;
    an injection needle connected to the distal end of the movable tube so that the movable tube and the injection needle move together as a unit, the injection needle extending in a distal direction from the distal end of the movable tube, the injection needle possessing a sharp distal end, the needle including a lumen having a rear end opening which opens into the hollow interior of the movable tube and a tip end opening at the sharp distal end of the needle from which the medicinal liquid is ejected;
    a plunger in the hollow interior of the movable tube and movable in the distal direction toward the distal end of the movable tube to deliver the medicinal liquid in the movable tube into the lumen of the injection needle;
    a sealing material at the distal end of the support tube, fixed within the lower end of the hollow interior of the support tube, the sharp distal end of the injection needle being embedded in the sealing material so the tip end opening of the lumen of the injection needle is closed by the sealing material to prevent the medicinal fluid in the movable tube from flowing out the tip end opening of the lumen of the injection needle;
    the movable tube being movable within the hollow interior of the support tube to move in a distal direction relative to the support tube from an initial position in which the sharp distal end of the injection needle is embedded in the sealing material to a puncture position in which the sharp distal end of the injection needle is positioned distally of the sealing material and distally of the end face of the support tube to puncture the skin; and
    a stopper provided on at least one of the support tube and the movable tube which stops the movement of the movable tube in the distal direction relative to the support tube so the movable tube is at the puncture position.

2. The injector according to claim 1, wherein the end face of the support tube possesses a through hole coaxially aligned with the injection needle, the sealing material covering the through hole.

3. The injector according to claim 1, wherein one of the movable tube and the support tube includes circumferentially spaced apart and axially extending ribs, the other of the movable tube and the support tube including axially extending grooves, the ribs being positioned in the grooves to guide the movement of the movable tube relative to the support tube.

4. The injector according to claim 1, wherein the end face of the support tube is comprised of a flange, the flange covering the hollow interior of the support tube at the distal end of the support tube, the flange possessing a through hole communicating with the hollow interior of the support tube and coaxial with the injection needle, the sealing material contacting the flange.

5. The injector according to claim 4, further comprising a pressure-sensitive adhesive on a surface of the flange facing away from the hollow interior of the support tube.

6. The injector according to claim 4, wherein a portion of the flange surrounding the through hole is protuberant in a direction away from the hollow interior of the support tube.

7. The injector according to claim 1, further comprising a pin positioned in a hole in the movable tube and in a hole in the support tube to fix the movable tube in the initial position relative to the support tube so that the movable tube in the initial position is immovable relative to the support tube.

8. The injector according to claim 1, comprising a first holder holding the plunger and a second holder holding the movable tube, the first and second holders being fixed to one another to fix the plunger relative to the movable tube in the initial position so that the sharp distal end of the injection needle remains embedded in the sealing material.

9. The injector according to claim 1, wherein the injection needle possesses a central axis non-perpendicularly oriented relative to the end face of the support tube.

10. An injector comprising:
a support tube possessing an end face to be pressed against skin;
a movable tube positioned in the support tube and advanceable in the support tube toward the skin;
an injection needle provided with a lumen, the lumen having a rear end opening at a rear end of the needle which communicates with the movable tube and a tip end opening at a tip end of the opening from which medicinal liquid is to be ejected;
a plunger positioned in the movable tube and advanceable in the movable tube toward the skin to cause medicinal liquid in the movable tube to be guided into the injection needle;
a sealing material fixed within a distal end of the support tube and penetrable by the injection needle;
a stopper limiting advancement of the movable tube in the support tube to a predetermined position,
wherein the tip end opening of the injection needle is sealed by the sealing material in an initial state of the injector so as to prevent medicinal liquid from being ejected therethrough.

11. The injector according to claim 10 wherein one of the movable tube and the support tube includes circumferentially spaced apart and axially extending ribs, the other of the movable tube and the support tube including axially extending grooves, the ribs being positioned in the grooves to guide movement of the movable tube relative to the support tube.

12. The injector according to claim 10, wherein the end face of the support tube is comprised of a flange, the flange possessing a surface constituting the end face which is pressed against the skin, the flange possessing a through hole which opens into the support tube, the sealing material contacting the flange and covering the through hole.

13. The injector according to claim 12, wherein a pressure-sensitive adhesive is provided on the surface of the flange.

14. The injector according to claim 12, wherein a portion of the flange surrounding the through hole is protuberant in a direction away from the movable tube.

15. The injector according to claim 10, comprising fixing means for fixing the movable tube to the support tube in the initial state to prevent movement of the movable tube relative to the support tube.

16. The injector according to claim 10, comprising fixing means for fixing the plunger to the movable tube in the initial state to prevent movement of the plunger relative to the movable tube.

17. The injector according to claim 10, wherein a tip face of the support tube is non-perpendicular to an axial direction of the support tube so that when the support tube contacts the skin, the support tube is obliquely oriented relative to the skin.

18. A method of operating an injector which is in an initial position, the injector in the initial position comprising a movable tube movably positioned in a support tube, an injection needle fixed to the movable needle to move together with the movable needle, a plunger positioned in the movable tube, medicinal fluid in the movable tube, and a sealing material fixed within a distal end of the support tube, wherein the injection needle possesses a sharp distal end and a distal end opening which opens into a lumen communicating with the medicinal fluid in the movable tube, and the sharp distal end of the injection needle being embedded in the sealing material so the distal end opening of the lumen of the injection needle is closed by the sealing material to prevent the medicinal fluid in the movable tube from flowing out the distal end opening of the lumen of the injection needle in the initial position; the method comprising:
pressing a distal end face of the support tube against skin to be punctured;
moving the movable tube in a distal direction relative to the support tube to cause the sharp distal end of the injection needle to move in the distal direction, pass completely through the sealing material so that the distal end opening is no longer closed by the sealing material, and extend distally beyond the distal end face of the support tube to puncture the skin; and
moving the plunger in the distal direction relative to the movable tube to force the medicinal fluid in the movable tube into the injection needle and to thereby inject the medicinal fluid in the skin.

19. The method according to claim 18, wherein in the initial position, the movable tube is fixed to the support tube so the movable tube is unable to be moved relative to the support tube, the method further comprising, before moving the movable tube in the distal direction relative to the support tube, unfixing the movable tube relative to the support tube.

20. The method according to claim 18, wherein the movable tube is moved in the distal direction relative to the support tube until a portion of the movable tube contacts a stop preventing further movement of the movable tube in the distal direction.

* * * * *